United States Patent [19]

Mertens et al.

[11] Patent Number: 5,408,019

[45] Date of Patent: Apr. 18, 1995

[54] CROSS-LINKED, WATER-ABSORBING POLYMER AND ITS USE IN THE PRODUCTION OF HYGIENE ITEMS

[75] Inventors: Richard Mertens, Krefeld; Kurt Dahmen, Mönchengladbach-Rheydt; Helmut Brehm, Krefeld, all of Germany

[73] Assignee: Chemische Fabrik Stockhausen GmbH, Krefeld, Germany

[21] Appl. No.: 191,742

[22] Filed: Feb. 1, 1994

Related U.S. Application Data

[63] Continuation of Ser. No. 946,360, Nov. 5, 1992, abandoned.

[30] Foreign Application Priority Data

May 11, 1990 [DE] Germany .................. 40 15 085.2

[51] Int. Cl.$^6$ .................... C08F 236/22; C08F 236/70
[52] U.S. Cl. .................... 526/240; 526/287; 526/371; 526/310; 526/312; 526/220
[58] Field of Search .............. 526/240, 307.1, 310, 526/312, 220, 287

[56] References Cited

U.S. PATENT DOCUMENTS

| | | | |
|---|---|---|---|
| Re. 32,649 | 4/1988 | Brandt et al. | 604/368 |
| 4,286,082 | 8/1981 | Tsubakimoto et al. | 526/240 |
| 4,833,222 | 5/1989 | Siddal et al. | 526/200 |
| 4,914,170 | 4/1990 | Chang et al. | 526/240 |
| 5,106,929 | 4/1992 | Ahmed et al. | 526/240 |

OTHER PUBLICATIONS

"Houben–Weyl: Methoden der Organischen Chemie", vol. 14/11, p. 265.

*Primary Examiner*—Mark Nagumo
*Attorney, Agent, or Firm*—Sprung Horn Kramer & Woods

[57] ABSTRACT

The invention relates to a cross-linked, water-absorbent polymer obtainable by the polymerization of a mixture consisting of a) 60–99%-wt. unsaturated, polymerizable monomers with acid groups which are neutralized to the extent of at least 30 mol-%, b) 0–37%-wt. monomers copolymerizable with a), c) 0.1–3.0%-wt. of a cross-linking agent and d) 0–10%-wt. of a water-soluble polymer, in which polymerization is conducted with a redox catalyst system containing formamidine sulfinic acid as reducing agent. The polymer is distinguished by a retention of greater than or equal to 28 g 0.9% aqueous NaCl-solution per 1 g of polymer, an absorption of greater than or equal to 26 g 0.9% aqueous NaCl-solution per 1 g of polymer at a load of 20 g/cm$^2$ and a residual monomer content of less than 700 ppm, and preferably less than 500 ppm. The invention also relates to the use of this polymer in the production of hygiene articles.

7 Claims, No Drawings

CROSS-LINKED, WATER-ABSORBING POLYMER AND ITS USE IN THE PRODUCTION OF HYGIENE ITEMS

This application is a continuation of application Ser. No. 07/946,360, filed Nov. 5, 1992, now abandoned.

The present invention relates to a cross-linked polymer which absorbs aqueous liquids; the polymer exhibits improved properties with regard to swelling and its capability of retaining aqueous liquids under load and has a very low content of residual monomers and a high gel rigidity in swollen condition. The present invention further relates to the use of said polymers in the production of hygiene articles.

These water-absorbing polymers find a great variety of uses. For instance, they are employed in diapers, articles for adult incontinence, cable sheathings, cleaning clothes, or they are used in soil conditioning.

These polymers are mainly used to absorb fluids which are produced or present within the body, in particular urine, and are therefore employed in diapers and adult incontinence articles. Up to the present, starch-acrylic-acid-graft-polymers and cross-linked acrylic-acid-salt-polymers have proved to be particularly suitable for this application, such as those known from U.S. Pat. No. 4,076,663 or EP [European Patent] No. 0036463.

Whereas water-absorbing polymers with a very high swelling capacity on contact with liquids, also referred to as the free swell capacity, were preferred in the production of diapers in the past, polymers with completely different properties are required today.

When it was realized that the water-absorbing polymers within the diaper are exposed to mechanical load caused by movements of the person wearing the diaper, new requirements have been stipulated for the polymers, that is high retention, i.e., high capability of retaining aqueous liquids, and a high absorption of aqueous liquids under load. In addition—for toxicological reasons—the polymers shall exhibit a low residual monomer content and a low content of extractable portions.

Since both concentration and kind of cross-linking agent as well as the polymerization catalysts strongly influence said four properties in water-absorbing polymers, the production of a polymer exhibiting a high retention, a high absorption under load, a low content of residual monomers, and small amounts of extractable portions involves great difficulties.

While a high retention can only be achieved in a slightly cross-linked polymer, a high absorption under load requires a highly cross-linked, stable polymer which can swell against the external pressure only on the basis of this stability. However, with an increasing degree of cross-linkage, the content of residual monomers increases at the same time, since the diffusion of the remaining monomer molecules towards the reactive radical centers is reduced due to the rapidly increasing viscosity of the polymer gel during its production. An undesired decrease in retention or an increase in the extractable portions are frequently caused by catalyst systems which reduce the residual monomers or by an increased catalyst concentration. The extractable portions of a crosslinked polymer are reduced with an increasing concentration of crosslinking agent.

EP No. 0083022 describes water-absorbent polymers having an extremely high free swell capacity and a low tendency to agglomerate. These polymers are produced by cross-linking the polymer particles with glycidyl ethers.

U.S. Pat. No. 4,535,098 describes water-absorbing polymers with moieties of hydrophobic comonomers and an improved gel stability.

According to EP No. 0205674 absorbing polymers are produced by polymerization of the acrylic acid in acid form and adjustment of the neutralization degree after termination of the polymerization. By this method polymers are obtained which have less soluble portions and an improved gel stability. Depending on the degree of cross-linking the retention is in the range of 20 to 74 g 0.9% NaCl-solution per 1 g of polymer. The excessive polymerization time and the expensive neutralization of the polymer gel are disadvantages of this method.

EP Nos. 0287970 and 0251314 describe UV- or electron irradiation, respectively, to achieve low contents of residual monomers in water-absorbing polymers.

DE-OS 3738602 describes swellable, water-absorbing graft polymers obtained by radical polymerization of—preferably—acrylic acid. However, according to this patent, neither formamidine sulfinic acid is used to manufacture improved water-absorbing polymers nor is there any indication with respect to retention, absorption under load, or residual monomer content of the described graft polymers.

DP 975794 describes the production of cation exchangers from insoluble polymers of the (meth)acrylic acid or the salts thereof; the trimeric addition product of formaldehyde to acrylonitrile is used as crosslinking agent. The trimeric addition product is N,N′, N″-trisacryloyl-hexahydrotriazine. According to this patent, the polymerization can be carried out with redox systems consisting of persulfates and sulfoxy-reducing agents; formamidine sulfinic acid is mentioned amongst others. Highly cross-linked polymers with low retention values are obtained. There are no indications with respect to conversion or residual monomer contents.

The known water-absorbent polymers do not provide the required property combination of high retention and high absorption under load, low content of residual monomers and small amounts of extractable portions.

It is accordingly the object of the present invention to provide a water-absorbing polymer exhibiting high retention and high absorption of aqueous liquids under load, as well as a low content of residual monomers and small amounts of extractable portions.

According to the present invention this object is achieved by a cross-linked, powdery polymer absorbing aqueous liquids or water, this polymer is obtained by polymerization of a mixture of a) 60.0 to 99.9%-wt. unsaturated, polymerizable monomers with acid groups which are neutralized to the extent of at least 30 mol-%, b) 0 to 37%-wt. water-soluble monomers copolymerizable with a), c) 0.1 to 3.0%-wt. of a cross-linking agent, and d) 0 to 10%-wt. of a water-soluble polymer with water as aqueous solution, size reduction, drying, and grinding of the formed polymer, characterized in that a multiply unsaturated monomer with at least one allylic unsaturated group or mixtures of polyvinyl and polyallyl compounds at a weight ratio of 1:≧0.6 are used as cross-linking agent according to c), and that the polymerization is carried out using a redox system consisting of formamidine sulfinic acid and one or several organic peroxides.

These polymers exhibit a retention of greater than or equal to 28 g 0.9% aqueous NaCl-solution per 1 g of polymer, an absorption of greater than or equal to 26 g 0.9% NaCl-solution per 1 g of polymer at a load of 20 g/cm$^2$, and a residual monomer content of less than 700 ppm, preferably less than 500 ppm, and a content of extractable portions of less than 6%.

It is known to use formamidine sulfinic acid combined with peroxides to <u>initiate</u> the polymerization (cf. Houben-Weyl, "Methoden der organischen Chemie", volume 14/1, page 265); however, surprisingly, it was found that the polymerization in the presence of the redox-catalyst-system formamidine sulfinic acid/peroxide results in a very high conversion rate of the monomers into polymers und that the residual monomer content in the polymer amounts to <700 ppm. In addition, it could not be foreseen that the retention of the water-absorbent polymers is not deteriorated but—on the contrary—influenced positively, and that the polymers also exhibit a high absorption under load.

The water-absorbing polymer is composed by 60 to 99.9%-wt. of unsaturated, polymerizable monomers with acid groups, e.g., acrylic acid, methacrylic acid, 2-acrylamido-2-methylpropane sulfonic acid and mixtures of these monomers; the acid groups are neutralized to the extent of at least 30 mol-%, e.g., as salt of sodium, potassium or ammonium.

The water-absorbing polymers may comprise as further monomers 0 to 37%-wt. of acrylamide, methacrylamide, hydroxyethyl acrylate, dimethylaminopropyl acrylate, dimethylaminopropyl acrylamide, or acrylamidopropyl trimethylammonium chloride. More than 37% of these monomers will deteriorate the swellability of the polymers.

The multiply unsaturated monomers with at least one allylic unsaturated group according to claim 1 are selected from the compound classes:

a) allyl esters, e.g., triallyl citrate, diallyl maleinate, allyl(meth)acrylate,
b) polyallyl ethers, e.g., glycerol triallyl ether, polyalkylene glycol ether of the allyl glycidic ether,
c) allyl amides, e.g., N,N'-diallyl succinic acid diamide, N,N,N',N'-tetraallyl oxalic acid diamide, N-allyl acrylamide, N-diallyl(meth)acrylamide, or
d) polyallyl amines, e.g., triallyl amine, tetraallyl ammonium chloride, methyl triallyl ammonium chloride, N,N'-tetraallyl ethylenediamine, N,N'-tetraallyl butanediamine.

0 to 10%-wt. of partially or completely saponified polyvinyl alcohol, polyvinylpryrrolidone, starch or starch derivatives may be contained in the water-absorbing polymer as water-soluble polymers. The molecular weight of these polymers is not critical as long as they are water-soluble.

The polymerization is carried out as solvent polymerization either in batches or continuously. For this purpose, the monomers and the cross-linking agent are dissolved in water so that the monomer concentration of the polymerizing mixture amounts to 20 to 35%; the desired neutralization degree is adjusted by addition of a base, the neutralization degree shall amount to at least 30 mol-%. Wetting agents may optionally be added to the monomer solution.

The polymerization may also be carried out in the disperse state as inverse suspension or emulsion polymerization.

According to the present invention, the polymerization is carried out with a redox-catalyst-system comprising formamidine sulfinic acid as the reducing component and organic peroxides as oxidizing component. Cumene hydroperoxide and tertiary butyl hydroperoxide are preferred because of their water-solubility.

The formamidine sulfinic acid may also be formed "in situ" from thiourea and hydrogen peroxide. "In situ" is to be understood in such a way that thiourea and hydrogen peroxide instead of formamidine sulfinic acid are added to the monomer solution and that the thiourea is oxidized in the monomer solution to form formamidine sulfinic acid.

The amount of the redox catalyst is in the usual range and amounts to about 100 to 2000 ppm formamidine sulfinic acid, relative to monomer solution, and to 100 to 4000 ppm peroxide.

In addition to formamidine sulfinic acid a second reducing agent may be used in an amount of up to 10%wt., relative to formamidine sulfinic acid, examples thereof include ascorbic acid, sulfite, dihydroxy-maleic acid, or hydroxylamine.

Azo compounds, such as azo bisamidinopropane-hydrochloride, may be used as further components of the polymerization catalysis.

The polymerization may be initiated by the formamidine sulfinic acid or by its alkali salts, or by means of a co-reducing agent or UV-light.

After polymerization, the polymer gel is reduced in size, dried, and screened to the desired particle size.

For the purpose of characterizing the water-absorbing polymers, the polymer powder is screened out to 100–850 µm, and this fraction is then optionally mixed with 0.1 to 1.0% of a fumed silica, preferably with 0.5% Aerosil 200; subsequently, retention, absorption under load, and content of residual monomers and extractable proportions are measured.

The retention is determined according to the tea bag test method and reported as average value of three measurements: approximately 200 mg polymer are enclosed in a tea bag and immersed in 0.9% aqueous NaCl-solution for 10 minutes. Then the tea bag is centrifuged at 1400 rpm in a centrifuge for 5 minutes and weighed. One tea bag without water-absorbing polymer is used as blank.

$$\text{Retention} = \frac{\text{Weight} - \text{blank reading}}{\text{Initial weight}} \, (g/g)$$

The absorption under load was determined with a Demand-Absorbency testing device (cf. "Allgemeiner Fließstoff-Report" 5/82, page 210–218), the test desk was substituted for a Büchner funnel. The Büchner funnel is 6.0 cm in diameter and adjusted such that the fluid level is on the level of the ceramic filter plate. A surface-ground cylinder having a diameter of 5.9 cm is used as punch the weight of which exerts a pressure of 20 g/cm$^2$.

For measuring purposes round filter paper is placed in the Büchner-funnel and 0.85 g of water-absorbing polymer of the size fraction 300 to 600 µm is evenly sprinkled thereon. Subsequently, the cylinder is inserted and the liquid stopping device opened. 0.9% aqueous NaCl-solution is used as test liquid. After one hour, the liquid absorption is read from the burette as consumption.

The residual monomer content in the water-absorbing polymers is determined by HPLC. To determine the soluble portion, the water-absorbing resin is stirred in 0.9% NaCl-solution for one hour, then it was filtered and the content of acid groups measured in the filtrate.

EXAMPLE 1

An aqueous acrylic acid solution comprising 0.5% diallyl acrylamide, relative to acrylic acid, was neutralized with sodium hydroxide solution under cooling. The acrylic acid concentration of the monomer solution amounted to 30%, the neutralization degree to 70%. 850 g of the monomer solution was cooled to 10° C. and purged with nitrogen for 10 minutes. Subsequently, 3 g tertiary butyl hydroperoxide, 4.5 mg ascorbic acid, dissolved in 10 g water, and 500 mg formamidine sulfinic acid, dissolved in 20 g water, was added. Polymerization started immediately, this could be recognized by a temperature elevation of the monomer solution. After 30 minutes, the obtained polymer gel block was crumbled and dried in hot air at 150° C.

Subsequently, the polymer was ground, screened out to 100 to 850 μm and mixed with 0.5% Aerosil 200. The water-absorbing polymer exhibited the following properties:
Retention: 29 g/g
Absorption under load: 27 g/g
Content of resid. monomers: 255 ppm
Extractable portion: 4.9%

EXAMPLE 2

2.5 g tertiary butyl hydroperoxide and 500 mg formamidine sulfinic acid, dissolved in 30 g buffer solution of pH 8, were mixed to 850 g monomer solution according to Example 1, except that 0.55 % diallyl acrylamide had been used. Polymerization started immediately. After 30 minutes, the resulting block of polymer gel was crumbled and dried at 150° C. in hot air.

The polymer was ground, sieved out to 100 to 850 μm and mixed with 0.5% Aerosil 200. The water-absorbent polymer had the following properties:
Retention: 29 g/g
Absorption under load: 26 g/g
Residual monomer content: 390 ppm
Extractable portion: 4.4%

EXAMPLE 3

850 g monomer solution according to Example 2 was mixed with 2.5 g tertiary butyl hydroperoxide and 400 mg formamidine sulfinic acid which was neutralized with sodium hydroxide solution by 10 mol-% and dissolved in 30 g water. The polymerization started immediately. The resulting polymer gel block was worked up into a water-absorbing polymer as described in Example 2.
Retention: 31.5 g/g
Absorption under load: 27.0 g/g
Residual monomer content: 370 ppm
Extractable portion: 5.0%

EXAMPLE 3

An aqueous solution of acrylic acid comprising 0.9% triallyl amine, relative to acrylic acid, was neutralized to the extent of 70 mol-% with potassium hydroxide solution under cooling; the acrylic acid concentration amounted to 28%.

850 g of the monomer solution was cooled to 10° C. and purged with nitrogen for 10 minutes. Subsequently, 3 g tertiary butyl hydroperoxide, 500 mg formamidine sulfinic acid, dissolved in 20 g water, and 4.5 mg ascorbic acid, dissolved in 10 g water, was added. Polymerization started immediately. After 30 minutes, the obtained polymer gel block was worked up into a water-absorbing polymer as outlined in Example 1.
Retention: 29.5 g/g
Absorption under load: 27.0 g/g
Residual monomer content: 290
Extractable portion: 4.5%

COMPARATIVE EXAMPLES 5 TO 8

The properties of four water-absorbing polymers, distributed by Norsolor, Dow Chemical, Allied Colloids, and Chemische Fabrik Stockhausen, are listed in Table I. They are cross-linked, partially neutralized polyacrylates.

TABLE I

| | Retention g/g | Absorption under load g/g | Residual monomer content ppm |
|---|---|---|---|
| Norsocryl B | 32 | 18 | 130 |
| Drytech 510 | 33 | 12 | 560 |
| Salsorb 90 P | 28 | 21 | 500 |
| Favor SAB 922 | 39 | 9 | 350 |

EXAMPLES 9 TO 12

Aqueous acrylic acid solutions were neutralized with varying amounts of sodium hydroxide solution and polymerized in accordance with Example 1. Table II shows the polymerization conditions and the properties of the water-absorbing polymers.

TABLE II

| Example | acrylic acid concentration | neutralization degree | TAA | ascorbic acid | t-BHP |
|---|---|---|---|---|---|
| 9 | 25% | 70% | 0.8% | 2 mg | 3.0 g |
| 10 | 30% | 50% | 0.9% | 4 mg | 2.5 g |
| 11 | 28% | 90% | 0.8% | 9 mg | 2.0 g |
| 12 | 30% | 70% | 1.0% | 4 mg | 2.5 g[1] |

| Example | FAS | Retention | Absorpt. under load | Residual monomer content | Extr. portion |
|---|---|---|---|---|---|
| 9 | 250 mg | 32 g/g | 29 g/g | 380 ppm | 5.5% |
| 10 | 500 mg | 31 g/g | 27 g/g | 220 ppm | 4.7% |
| 11 | 500 mg | 28 g/g | 26 g/g | 430 ppm | 4.7% |
| 12 | 500 mg | 30 g/g | 29 g/g | 330 ppm | 3.9% |

[1] 2.5 g of cumene hydroperoxide instead of tertiary butyl hydroperoxide were used in Example 12.
TAA = triallyl amine
t.-BHP = tertiary butyl hydroxyperoxide
FAS = formamidine sulfinic acid

EXAMPLES 13 TO 17

Acrylic acid (AcA) was copolymerized in aqueous solution in the presence of 1% triallyl amine with methacrylic acid (MAA), acrylamide (AA), 2-acrylamido-2-methylpropane sulfonic acid (AMPS) or dimethylaminopropyl acrylamide (DIMAPA). The monomer concentration amounted to 30%, the neutralization degree to 70%. 9 mg ascorbic acid, 3 g tertiary butyl hydroperoxide, and 500 mg formamidine sulfinic acid were used as catalyst system; Table III shows the copolymer composition and the properties of the water-absorbing polymers:

TABLE III

| Example | AcA %-wt. | Comonomer %-wt. | Retention |
|---|---|---|---|
| 13 | 90 | 10 AMPS | 31.5 g/g |
| 14 | 65 | 35 AMPS | 30.5 g/g |
| 15 | 75 | 25 AA | 30.0 g/g |
| 16 | 70 | 30 MAA | 29.0 g/g |
| 17 | 90 | 10 DIMAPA | 31.0 g/g |

| | Absorption | Residual | Extractable |

TABLE III-continued

| Example | under load | monomer content | portion |
|---|---|---|---|
| 13 | 29.5 g/g | 380 ppm | 3.5% |
| 14 | 28.5 g/g | 290 ppm | 2.0% |
| 15 | 28.0 g/g | 370 ppm | 2.2% |
| 16 | 28.0 g/g | 220 ppm | 4.8% |
| 17 | 28.0 g/g | 240 ppm | 5.2% |

COMPARATIVE EXAMPLES 18 TO 23

850 g monomer solution with 30% acrylic acid neutralized to the extent of 70 mol-% was initiated with various catalysts; the catalysts and the properties of the obtained water-absorbing polymers are listed in Table IV.

TABLE IV

| Example | TAA % | ascorbic acid | t-BHP | SPS | $H_2O_2$ | ABAH |
|---|---|---|---|---|---|---|
| 18 | 1.0 | 9 mg | 3 g | | | |
| 19 | 1.0 | 9 mg | 3 g | | | 1 g |
| 20 | 1.0 | 9 mg | 3 g | 0.6 g | | |
| 21 | 1.0 | 9 mg | | 0.6 g | 50 mg | |
| 22 | 0.9 | | 2 g | | | |
| 23 | 0.8 | | 2 g | | | |

| Example | SPS = sodium peroxidisulfate dithionite | formaldehyde-sulfoxylate | Retention |
|---|---|---|---|
| 18 | | | 27 g/g |
| 19 | | | 29 g/g |
| 20 | | | 25 g/g |
| 21 | | | 25 g/g |
| 22 | 0.5 g | | 30 g/g |
| 23 | | 100 mg | 31 g/g |

| Example | Absorption under load | Residual monomer content | Extractable portion |
|---|---|---|---|
| 18 | 22 g/g | 3.380 ppm | 4.1% |
| 19 | 29 g/g | 2.430 ppm | 5.1% |
| 20 | 27 g/g | 1.960 ppm | 5.6% |
| 21 | 27 g/g | 1.490 ppm | 5.6% |
| 22 | 26 g/g | 6.200 ppm | 6.2% |
| 23 | 22 g/g | 9.110 ppm | 4.9% |

EXAMPLES 24 TO 32

Various cross-linking agents were added to 850 g monomer solution with 30% acrylic acid which had been neutralized to 70 mol-% by sodium hydroxide solution. As described in Example 1, the polymerization was then initiated with 4.5 mg ascorbic acid, dissolved in 10 g water, 3 g tertiary butyl hydroperoxide, and 500 mg formamidine sulfinic acid, dissolved in 20 g water. The properties of the obtained water-absorbing polymers are listed in Table V:

TABLE V

| Example | Cross-linking agent | Retention |
|---|---|---|
| 24 | 0.8% TMPTA | 30 g/g |
| 25 Comparison | 1.2% TMPTA | 29 g/g |
| 26 | 0.5% TMPTA/0.4% TAA | 28 g/g |
| 27 | 0.5% TMPTA/0.8% TAC | 29 g/g |
| 28 Comparison[1] | 11.1% N-trisacryloyl-hexahydrotriazine | 9 g/g |
| 29 Comparison[2] | 0.3% N-trisacryloyl-hexahydrotriazine | 24 g/g |
| 30 | 0.25% MBA/0.25% TAA | 28 g/g |
| 31 | 1.0% N,N'-tetraallyl butanediamine | 31 g/g |
| 32 | 0.5% N-allyl acrylamide | 28 g/g |

| Example | Absorption under load | Residual monomer content | Extractable portion |
|---|---|---|---|
| 24 | 17 g/g | 210 ppm | 12.3% |
| 25 Comparison | 18 g/g | 340 ppm | 11.0% |
| 26 | 26 g/g | 405 ppm | 5.8% |
| 27 | 27 g/g | 470 ppm | 5.6% |
| 28 Comparison[1] | 10 g/g | 8.1% | 0.8% |
| 29 Comparison[2] | 24 g/g | 6.9% | 2.2% |
| 30 | 26 g/g | 290 ppm | 5.8% |
| 31 | 28.5 g/g | 390 ppm | 4.3% |
| 32 | 28 g/g | 230 ppm | 3.8% |

TMPTA = trimethylolpropane triacrylate
TAA = triallyl amine
TAC = triallyl citrate
MBA = methylene bisacrylamide
[1]Example 28 was produced according to example 1 of DP 975794
[2]Example 29 was produced using 0.35 g formamidine sulfinic acid/0.5 g persulfate/9 mg ascorbic acid.

EXAMPLE 33

850 ml monomer solution according to Example 1 with 1% triallyl amine instead of diallyl acrylamide and additionally comprising 6.7 g dissolved polyvinyl alcohol was polymerized as in Example 1 and processed to form a water-absorbing polymer comprising 2% polyvinyl alcohol.
Retention: 30 g/g
Absorption under load: 29 g/g
Residual monomer content: 370 ppm
Extractable portion: 3.9%

EXAMPLE 34

An aqueous acrylic acid solution comprising 0.7% triallyl amine was neutralized with sodium hydroxide solution under cooling; an aqueous starch solution (type: Sorbex 222 of Südstärke GmbH, FRG) was added then. The acrylic acid concentration amounted to 26.5% and the neutralization degree to 70 mol-%. 935 g of this monomer solution was cooled to 10° C., purged with nitrogen for 10 minutes, and mixed with 3 g tertiary butyl hydroperoxide, 500 mg formamidine sulfinic acid, dissolved in 20 g water, and 4.5 mg ascorbic acid, dissolved in 10 g water. The polymerization started immediately. After 30 minutes the obtained gel block was crumbled and dried at 110° C. with hot air. The dry polymer comprises 8.5% starch.
Retention: 30.5 g/g
Absorption under load: 27.5 g/g
Residual monomer content: 310 ppm
Extractable portion:

EXAMPLE 35

850 g monomer solution of Example 1 but with 1% triallyl amine instead of diallyl acrylamide was cooled to 10° C. and purged with nitrogen for 10 minutes. Subsequently, 0.35 g thiourea, dissolved in 20 g water, 1.0 g hydrogen peroxide, 3 g tertiary butyl hydroperoxide, and 5 mg ascorbic acid, dissolved in 10 g water, was added to the monomer solution according to the given order, whereupon the polymerization started immediately. After 30 minutes, the resultant polymer gel block was crushed and dried at 150° C. with hot air.
Retention: 28 g/g
Absorption under load: 28 g/g
Residual monomer content: 400 ppm
Extractable portion: 4.3%

The use of the water-absorbing polymers according to the present invention was tested in sandwiched constructions consisting of fluff and water-absorbing polymer. Round constructions consisting of 3 fluff layers and 2 layers of water-absorbing polymer (diameter: 5.8 cm) were placed in the Büchner funnel determining the absorption under load. At a pressure load of 20 g/cm² the constructions are allowed to suck 0.9% NaCl-solution for 150 minutes, then the absorption of the water-absorbent polymer is calculated as follows:

$$\text{Absorption} = \frac{(\text{consumption in burette}) - \text{blank for fluff}}{\text{Initial weight}}$$

TABLE VI

Application Examples 36 to 41:

| Example | Polymer of Example | Portion Polymer (1) in construction | Absorption (ml/g) |
| --- | --- | --- | --- |
| 36 | 1 | 20 | 35 |
| 37 | 1 | 40 | 31 |
| 38 | 12 | 20 | 36 |
| 39 | 12 | 40 | 32 |
| 40 | 33 | 20 | 35 |
| 41 | 33 | 40 | 31 |

| Comparative Example | | | |
| --- | --- | --- | --- |
| FAVOR SAB 922 (2) | | 20 | 29 |
|  | | 40 | 25 |
| FAVOR SAB 954 (2) | | 20 | 29 |
|  | | 40 | 27 |

(1) %-wt., relative to fluff
(2) Commercial products of Chemische Fabrik Stockhausen GmbH It is preferred to use the polymers according to the present invention for the production of constructions which are capable of absorbing body liquids and which are suitable for the use in diapers and hygienic articles and consist of 98 to 30%-wt. hydrophilic fibers and 2 to 70%-wt. water-absorbing polymers.

We claim:

1. A cross-linked, powdery polymer absorbing aqueous liquids or water, obtained by polymerizing a mixture consisting of a) 60.0 to 99.9%-wt. unsaturated, polymerizable monomers with acid groups which are neutralized to the extent of at least 30 mol-%,
b) 0 to 37%-wt. water-soluble monomers copolymerizable with a),
c) 0.1 to 3. 0%-wt. of a cross-linking agent, and
d) 0 to 10%-wt. of water-soluble polymers, with water as aqueous solution, crumbling, drying, and grinding the formed polymer,
characterized in that a multiply unsaturated monomer with at least one allylically unsaturated group or mixtures of polyvinyl and polyallyl compositions at a weight ratio of 1:≧0.6 is used as cross-linking agent according to c), and that the polymerization is carried out with a redox system comprising of formamidine sulfinic acid and one or more organic peroxides.

2. The cross-linked polymer absorbing aqueous liquids or water according to claim 1, characterized by a retention of greater than or equal to 28 g 0.9% aqueous NaCl-solution per 1 g of polymer, an absorption of greater than or equal to 26 g 0.9% aqueous NaCl-solution per 1 g of polymer under a load of 20 g/cm², a residual monomer content of less than 700 ppm, and a content of extractable portions in 0.9%-wt. NaCl aqueous solution of less than 6%-wt.

3. The cross-linked polymer absorbing aqueous liquids or water according to claim 1, wherein the redox catalyst system comprises further reducing agents in addition to formamidine sulfinic acid.

4. The cross-linked polymer absorbing aqueous liquids or water according to claim 1, wherein the formamidine sulfinic acid is formed "in situ" from thiourea and hydrogen peroxide.

5. The cross-linked polymer absorbing aqueous liquids or water according to claim 1, wherein acrylic acid, methacrylic acid, 2-acrylamido-2-methylpropane sulfonic acid or mixtures of said monomers are used as acid-groups-containing monomers.

6. The cross-linked polymer absorbing aqueous liquids or water according to claim 1, wherein polyvinyl alcohol, polyvinylpyrrolidone, starch or starch derivatives are used as water-soluble polymers.

7. A hygienic article including as an absorbent the cross-linked polymer according to claim 1.

* * * * *

UNITED STATES PATENT AND TRADEMARK OFFICE
CERTIFICATE OF CORRECTION

PATENT NO. : 5,408,019
DATED : April 18, 1995
INVENTOR(S) : Mertens, et al.

It is certified that error appears in the above-indentified patent and that said Letters Patent is hereby corrected as shown below:

Col. 10, line 15   Delete " of "

Signed and Sealed this

Fourth Day of July, 1995

Attest:

BRUCE LEHMAN

*Attesting Officer*        *Commissioner of Patents and Trademarks*